US 6,557,398 B2

(12) United States Patent
Lindmark et al.

(10) Patent No.: US 6,557,398 B2
(45) Date of Patent: May 6, 2003

(54) METHOD AND A DEVICE FOR DETERMINING THE LIQUID RETENTION OF ABSORBENT ARTICLES

(75) Inventors: Karin Lindmark, Gothenburg (SE); Christina Steger, Molndal (SE); Johan Granath, Vastra Frolunda (SE); Berith Porso, Partille (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/105,325

(22) Filed: Mar. 26, 2002

(65) Prior Publication Data

US 2002/0139177 A1 Oct. 3, 2002

Related U.S. Application Data
(60) Provisional application No. 60/279,118, filed on Mar. 28, 2001.

(51) Int. Cl.$^7$ ............................................. G01N 15/08
(52) U.S. Cl. ..................... 73/73; 73/76; 73/159; 68/242; 100/131
(58) Field of Search .................... 73/73, 74, 75, 73/76, 77, 38, 159; 68/242; 100/131

(56) References Cited

U.S. PATENT DOCUMENTS

| 4,676,079 A | * | 6/1987 | Czauderna | 100/116 |
| 5,361,627 A | * | 11/1994 | Levesque | 422/947 |
| 6,298,714 B1 | * | 10/2001 | Courtray | 73/38 |

* cited by examiner

Primary Examiner—Daniel S. Larkin
Assistant Examiner—David Rogers
(74) Attorney, Agent, or Firm—Young & Thompson

(57) ABSTRACT

A method of measuring the liquid retention of absorbent articles (20) of the kind that includes an absorbent body having a top side which lies proximal to the wearer's skin when the article is worn, and a bottom side which is covered by a liquid-impermeable backing sheet, wherein the method comprises the steps of applying a determined amount of liquid to a region on the top side of the article, urging a pressure body (1) against a region of the top side of the article with a given force, and collecting and measuring the amount of liquid pressed out from the top side of the article. The force with which the pressure body (1) is pressed against the top side of the article, is set selectively on a device (2–4) for pressing the pressure body against the top side of the article (20), and the liquid pressed from the top side of the article is transported to a measuring vessel (15) with the aid of sub-pressure.

10 Claims, 2 Drawing Sheets

METHOD AND A DEVICE FOR DETERMINING THE LIQUID RETENTION OF ABSORBENT ARTICLES

This application claims benefit of provisional application No. 60/279,118 filed Mar. 28, 2001.

FIELD OF INVENTION

The present invention relates to a method and also to a device for determining the liquid retention of absorbent articles, such as sanitary napkins, diapers, incontinence napkins and like articles.

DESCRIPTION OF THE BACKGROUND ART

In order for an article to be felt dry and comfortable when worn, a very important factor is the liquid retention of the article, in other words its ability to retain liquid that has been absorbed by the absorbent body or pad of the article, when the article is subjected to load. It has been found that the ability of the article to retain absorbed liquid at the greatest loads occurring in normal use of the article is a decisive factor in respect of many users as to whether or not the article is felt to be comfortable.

Absorbent articles are generally able to absorb large quantities of liquid and are most often designed to transport discharged liquid quickly away from the surface of the article. It is important with respect to wearer comfort that the article has a dry top surface and that the liquid acquisition properties of the article, i.e. its ability to receive and transport discharged liquid quickly away from the top surface and into the absorbent body is therefore highly significant to the comfort of the wearer.

One way of determining the liquid retention of the article is to measure the amount of liquid that exits from an article which contains absorbed liquid, when the article is subjected to load. In known retention measuring processes, a liquid-containing article is subjected to a weight applied on top of the article wherewith the volume of liquid pressed from the article is drawn up by suction through the capillary forces of a fibre body, normally filter paper, disposed between the weight and the article. The liquid retention of the article is determined by weighing the fibre body. One problem with these known methods is that the capillaries in filter paper may vary in size. Moreover, when it is necessary to use several filter papers, the interfaces between the papers create problems. It has also been found that the measuring results depend on the person carrying out the measuring process, in other words different people obtain different results for one and the same article. Consequently, the reproducibility or certainty of retention measurement values obtained with these known processes is inadequate. Moreover, the suction properties of the fibre body used is liable to change in storage (ageing) or for some other reason, which can influence the result of the measuring process.

Another problem is that the load to which an article is subjected during use varies widely. This means that a number of weights must be available for the retention test, if it is to be possible to test for all feasible loads. Moreover, in the case of the known methods retention is normally measured at relatively low loads. This fails to give a clear picture of the retention properties of an article, since it has been found that an article which has good retention at low loads can have poor retention at high loads. User tests have also shown that retention at high load, e.g. the load experienced when the wearer sits on a chair or on the saddle of a bicycle, is decisive in determining whether the article is felt to be comfortable or not. Thus, these known methods of measuring retention under relatively low loads are poorly adapted to reality, in other words as to how a wearer judges the retention of the article concerned.

An object of the present invention is to eliminate or at least considerably reduce these problems, and to provide a flexible method for measuring retention of absorbent articles that has good reproducibility and that can be readily carried out. Another object is to provide an apparatus for carrying out the method that can be easily handled and that enables measurements to be made with loads that are close to reality.

SUMMARY OF THE INVENTION

The former object is achieved in accordance with the invention with a method of measuring the retention of absorbent articles that include an absorbent body having a top side which lies proximal to the wearer's skin in use, and a bottom side which is covered by a liquid-permeable backing sheet, wherein the method comprises the steps of delivering a determined amount of liquid to one region on the top side of the article, urging a pressure body against a region on the top side of the article with a determined force, and collecting and measuring the amount of liquid therewith pressed from on the top side of said article, wherein the method is characterised by setting the determined force with which the pressure body is pressed against the top side of the article on a device that is adapted to urge the pressure body against the top side of said article with a selective pressure, and transporting the liquid pressed out from the top side of the article to a measuring vessel with the aid of sub-pressure.

According to one preferred embodiment of the invention, the liquid pressed from the top side of the article is transported to the measuring vessel via a space in the pressure body, this space communicating with the top side of the article via a liquid-permeable bottom of the pressure body. The device with which the pressure body is pressed against the top side of the article is conveniently computer controlled.

The invention also relates to a device for measuring retention of absorbent articles that include an absorbent body which has a top side that lies proximal to the wearer's skin in use, and a bottom side which is covered by a liquid-impermeable backing sheet, wherein the device includes a pressure body and means for collecting liquid that gathers beneath the bottom of the pressure body, and wherein the device is characterised in that the pressure body includes a perforated bottom and a space which is delimited downwardly by said perforated bottom; in that the device includes a liquid collecting vessel in connection with the space in the pressure body, means for generating a sub-pressure in the collecting vessel, means for measuring the amount of liquid present in the collecting vessel, and means for selectively setting the pressure exerted by the pressure body against the top side of an absorbent article placed on a fixed supportive surface centrally beneath the pressure body.

In one preferred embodiment, the device includes means for delivering liquid to the absorbent body of an absorbent article, and a computer for controlling the various means. The pressure body is preferably connected to an arm that can be moved by means of a stepping motor. The collecting vessel is connected to a space in the pressure body interior which, in turn, is connected to a sub-pressure source, and is removably connected to the pressure body with the aid of an air-tight coupling element.

In another embodiment, the pressure body is connected to the arm for pivotal movement about a horizontal axis.

BRIEF DESCRIPTION OF THE DRAWINGS

The present invention will now be described with reference to the accompanying drawings, in which.

DESCRIPTION OF EMBODIMENTS

Figure 1:
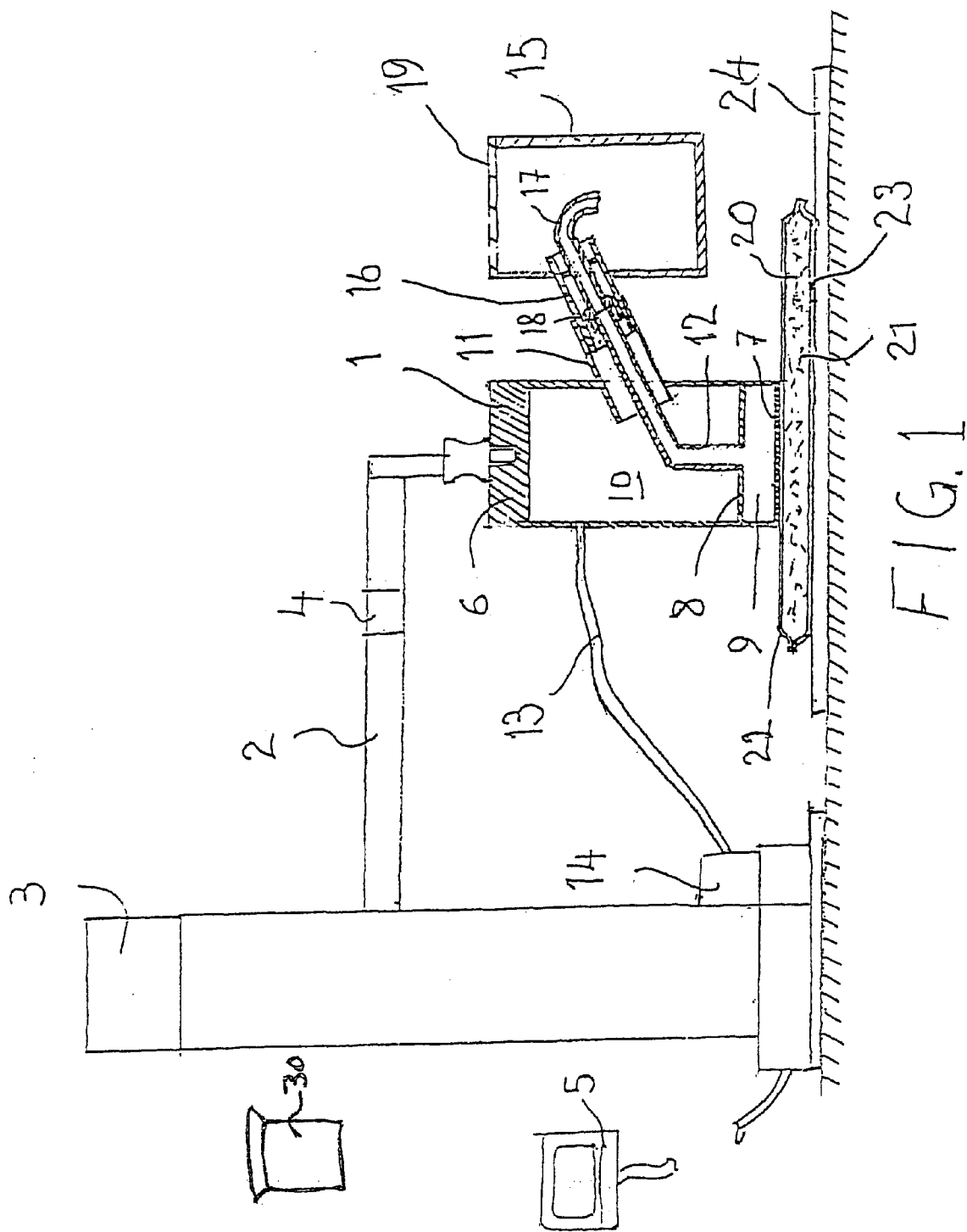
FIG. 1 is a schematic, partially sectioned side view of a liquid retention measuring device according to a first embodiment of the invention.

The retention measuring device illustrated schematically in FIG. 1 includes a pressure body 1 which is attached to an arm 2. The arm 2 can be moved linearly up and down with the aid of a screw-nut mechanism driven by a stepping motor 3. The arm 2 also includes a loading cell 4 which functions to sense the load acting on the arm. The stepping motor is controlled by a computer 5 which is programmed to enable the force at which the pressure body presses against an underlying supportive surface to be set selectively. The load cell 4 senses the load on the arm 2 continuously, therewith enabling the set pressure to be maintained during a measuring operation.

The pressure body 1 is comprised of a hollow cylinder made of transparent material, such as glass or Plexiglas for instance, and is closed at its upper end by an upper wall 6 secured in the arm 2, for instance screwed thereinto. The pressure body also has a perforated bottom 7 and a transverse wall 8 which is situated in the lower part of said body and which divides the interior space of said body into a lower chamber 9 and an upper chamber 10. A tubular body 11 is open at both ends and extends through an opening in the side wall of the upper chamber 10 and is fastened to the side wall in some suitable manner, e.g. glued thereto. The transverse wall 8 has a central opening into which the lower end of a pipe 12 opens out. The upper part of the pipe 12 extends inside the tubular body 11. The side wall of the upper chamber 10 includes a further opening into which a hose 13 opens out. The hose 13 passes to a vacuum pump 14 or to some other appropriate sub-pressure source.

The apparatus also includes a liquid container 15 which is removably connected to the pressure body 1 in a manner such as to connect the upper chamber 10 of the pressure body and the upper end of the pipe 12 with the interior of the liquid container 15 when said container is connected to the pressure body. In the case of the illustrated embodiment, the liquid container 15 comprises a tubular body 16 which is open at both ends and part of which projects out from the side wall of the container 15. The end of the part of the tubular body 16 that projects out from the side wall can be inserted into the end of that part of the tubular body 11 of the pressure body that projects out from the side wall of the pressure body. Extending within the tubular body 16 of the liquid container is a pipe 17 that has the same diameter as the pipe 12 in the pressure body. The pipe 17 is secured to the tubular body 16 in some suitable manner that will not prevent air from flowing in the space between the pipe 17 and the tubular body 16, for instance by means of three radial stays, braces or corresponding elements. The end of the pipe 17 located outwardly of the container interior has a collar 18 which sealingly embraces the upper end of the pipe 12 when the pressure body 1 and the liquid container 15 are interconnected. The outer diameter of the collar 18 is smaller than the inner diameter of the tubular body 16. Although not shown, the tubular body 16 also includes a sealing ring that ensures that the tubular bodies 11 and 16 are sealingly connected together in the assembled state of the pressure body and the liquid container, as shown in FIG. 1. In the illustrated embodiment, the tubular body 16 is inclined such that the bottom of the container 15 will be horizontal in the assembled state of the pressure body and liquid container. The liquid container 15 may also have a removable lid 19. Also shown in FIG. 1 is an absorbent article 20, which includes an absorbent body 21 enclosed between a liquid-permeable top sheet 22 and a liquid-impermeable backing sheet 23, said article being shown placed on a flat plate 24 centrally beneath the pressure body 1.

When using the described apparatus, the arm 2 is controlled to press the pressure body 1 against the absorbent article 20 at a determined pressure. At the same time, the vacuum pump is activated so as to generate a sub-pressure in the upper chamber 10 of the pressure body. This sub-pressure propagates to the interior of the liquid container 15, via the tubular bodies 11 and 16, and further into the lower chamber 9 of the pressure body, via the pipes 17 and 12. The liquid that is pressed out of the absorbent article by the load exerted via the pressure body is transported to the container 15 via the perforated bottom of the pressure body, the lower chamber 9 of said pressure body and the pipes 12, 17, with the aid of the sub-pressure prevailing in said container 15.

A suitable method of measuring the retention of an absorbent article by means of apparatus according to the present invention will now be described in detail. There is first chosen a desired measuring program on the computer 5 of the apparatus described with reference to FIG. 1. If the desired program is not preprogrammed in the computer, the values desired are written into the standard measuring program for which the computer has been programmed. The liquid container 15 is then uncoupled from the pressure body 1 and a weighing instrument (scales) is tared with the container, whereafter the container is re-connected to the pressure body.

The absorbent article is then weighed and its weight recorded. The article is then placed on a flat plate, so as to lie completely flat on the plate with the liquid-permeable top sheet facing upwards. A chosen amount of liquid, such as synthetic urine for instance, is then applied to the article by means of an appropriate dispenser 30. As a rule, the larger the article, the larger the amount of liquid that shall be applied. The liquid is normally applied to the wetting point of the article, i.e. to the region of the article into which liquid is normally discharged when the article is in use.

When the liquid dosage has been fully absorbed by the absorbent article, the flat plate carrying the article is placed beneath the pressure body 1 and the measuring device is activated in response to a command entered into the computer 5. The article may be positioned so that the region in which the liquid has been applied will be situated centrally beneath the pressure body, although other positions are conceivable for the purpose of investigating retention in regions other than the wetting point. Subsequent to activation of the measuring apparatus, the pressure body 1 is moved automatically to its starting position and the load cell 4 is tared to zero. After a chosen pre-programmed waiting period, the measuring process starts automatically, by generating a sub-pressure inside the pressure body 1, and therewith in the container 15, and by urging the pressure body against the article at a chosen pre-set force.

Because the chosen set pressure is controlled by the load cell 4, the load on the article will be constant (naturally within the degree of accuracy to which the apparatus can be adjusted) and the compression caused by the pressure forces on the article will be compensated by slight movements of the pressure body. As a result of the sub-pressure prevailing in the liquid container 15, liquid that has been pressed out from the surface of the article will be sucked into the container, via the liquid-permeable bottom of the pressure body, the lower chamber 9, and the pipes 12, 17. When the set measuring time has expired, the pressure body will return automatically to its starting position above the article and the sub-pressure facility switched off.

The liquid container 15 in which the liquid pressed from the article has been collected is then weighed. The weighing instrument is conveniently connected to the computer, so that the volume of liquid drawn by suction into the container can be directly indicated and stored, by dividing the measured value by the density of the liquid given in g/ml. The retention value is obtained by subtracting the former value from the amount of liquid delivered to the article.

The described method and the chosen parameters have been given solely by way of example. The inventive apparatus enables the parameters, e.g. pressure and times, to be chosen selectively, therewith enabling the apparatus to be used to measure retention at any desired load, simply by entering desired parameters into the computer. Varying loads can also be measured during one or more liquid applications. This constitutes a significant advantage over earlier known methods, in which the articles are loaded with weights and the liquid collected in filter bodies.

The method may, of course, also be used to determine the liquid retention of individual layers included in an absorbent body. The term absorbent article used in the claims also embraces such layers.

Figure 2:
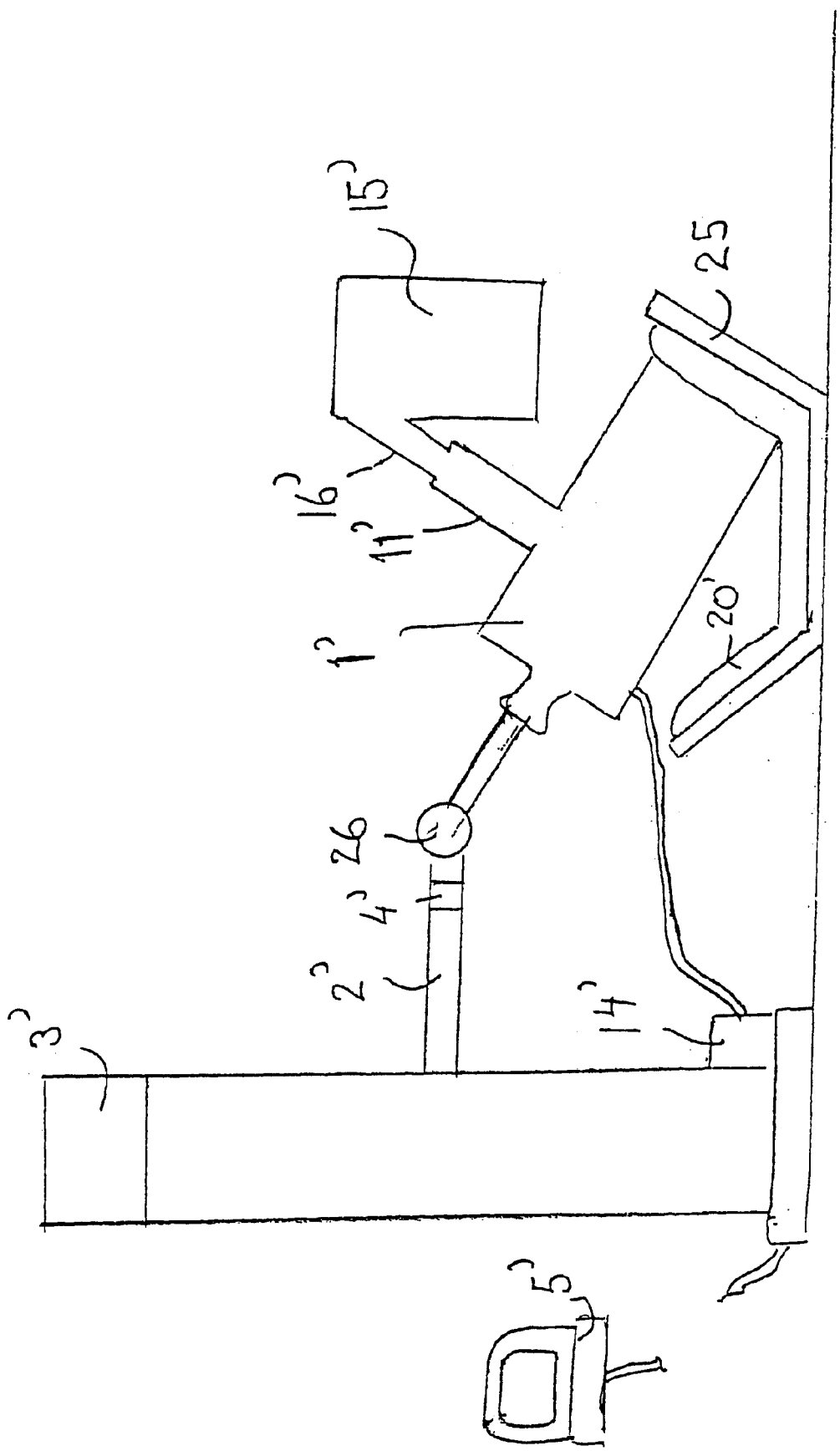
FIG. 2 is a schematic side view of a device according to a second embodiment of the invention.

FIG. 2 is a schematic illustration of a second embodiment of retention measuring apparatus. The sole differences between the apparatus shown in FIG. 2 and the apparatus shown in FIG. 1 are, in principle, that the article 20' is placed on a plate 25 whose front and rear portions are upwardly inclined and that the pressure body 1 is connected to the arm 2' by means of an adjustable pivot 26. Those components of the apparatus shown in FIG. 2 that find correspondence in the components of the apparatus shown in FIG. 1 have been given the same reference signs as those used in FIG. 1 but with the addition of a prime. Such an apparatus enables retention to be measured with articles whose front and rear portions are in the same positions as those that are normal when the article is worn by a user. In this case, the computer is programmed to calculate and control the pressure component that is directed along the longitudinal axis of the pressure body. The apparatus shown in FIG. 2 may, of course, also be used to measure the retention of a horizontal part of the article.

The method described has many advantages over earlier known retention measuring methods. Firstly, it eliminates totally the uncertainty associated with the use of the filter paper. Because liquid is applied and measuring carried out automatically, and is therefore not person dependent, tests have shown that the reproducibility or certainty achieved with the retention measuring process according to the described inventive method is two times as good as the reproducibility achieved when measuring according to a conventional measuring process. A further advantage is that the amount of liquid applied and the load to which the article is subjected can be chosen selectively in the absence of those limitations concerned with filter capacities and different fixed weights that curtail the options of known methods. Moreover, the measurements can be carried out in a manner which resembles the actual loads to which an article may be subjected, by choosing, without limitation, liquid quantities and wetting sequences that are in accord with actual article loading cases.

The possibility of subjecting the test article to loads that correspond to the highest loads occurring in normal use of an article have been found to be of decisive significance, as will be apparent from the following example for instance.

EXAMPLE

The liquid retention of two mutually different mild incontinence napkins A and B was measured in accordance with a known method and in accordance with the method described above.

In the case of the known method, the products A and B were weighed and the weights recorded. The products were then placed on a flat surface, whereafter 50 ml synthetic urine were applied to the wetting points of the two products A and B and the products then allowed to rest for 10 minutes, to enable the liquid to penetrate into the products. A filter paper, Munktell 1003, having a diameter of 55 mm was then placed above the wetting point of respective products. The filter papers had been weighed and their weights recorded prior to being placed on the products. A weight of 1800 g having a diameter of 55 mm was then placed on respective products, meaning that the products were loaded with about 7.9 kPa. The weights were removed after one minute, and the filter papers then weighed.

The conventional measuring process effected with a load of 7.9 kPa showed that retention was far better (more liquid remained in the product) with respect to product B than with respect to product A.

The liquid retention of products A and B was also measured in accordance with the inventive method. 70 ml liquid were applied to the products in this case. A pressure body 50 mm in diameter was used. The sub-pressure generated was 380 mbar and the load was 51 kPa. The waiting time was 5 minutes and the loading time 1 minute.

The result of this measuring process was the reverse of the aforesaid result, namely that the retention of product A was far better than the retention of product B.

A user test was also carried out with the two products. In this test, the users were asked to judge which of the products A and B felt the safest, had the driest surface and could absorb the most discharges, among other things. All of these parameters are related to whether or not the product is felt to be wet. The users felt that the product A was significantly better than the product B in respect of all of these parameters.

Thus, it is obvious that the retention of a product under high load is much more important to the apparent dryness and comfort of the product than its retention at low loads in respect of the majority of users. Because a minority of users preferred the product B, which had better retention at low loads, the liquid retention at low loads is of course also of interest in providing a product that suits all users. Consequently, it is highly beneficial when the retention of a product can be readily measured at both high and low loads by means of the inventive method.

It will be understood that the described and illustrated embodiments can be modified in many ways within the scope of the invention. In both of the described embodiments, the liquid container 15 is positioned with its bottom horizontal and could be provided with a scale in ml that will enable the amount of liquid drawn up by suction to be read-off directly. Furthermore, an optical level indicator may be provided for automatic reading and registering of the amount of liquid that has been drawn up by suction. The interior of the pressure body may be connected to a constant sub-pressure source via a valve that suitably opens automatically as the pressure body takes its starting position. The apparatus may also include a computer controlled, automatic dispensing device that delivers liquid to the article and that is moved from and to a dispensing position with the aid of a robotic arm or some corresponding means. Such a robotic arm may also be adapted to move the liquid container 15 between said weighing instrument and the pressure body. The robotic arm may also be adapted to move the liquid container to and from a station for emptying and drying said container. The pipes 12 and 17 and the tubular bodies 11 and 16 may also be interconnected in a way other than that shown and described. Although not preferred, it is also possible to allow the sub-pressure source to be coupled directly to the liquid container 15. Moreover, the pressure body may be moved by means other than a screw-nut mechanism, e.g. by means of an hydraulic cylinder. The invention is therefore solely limited by the contents of the accompanying claims.

What is claimed is:

1. A method of measuring the liquid retention of absorbent articles of the kind that includes an absorbent body having a top side which lies proximal to the wearer's skin when the article is worn, and a bottom side which is covered by a liquid-impermeable backing sheet, wherein the method comprises the steps of applying a determined amount of liquid to a region on the top side of the article, urging a pressure body against a region of the top side of the article with a given force, and collecting and measuring the amount of liquid pressed out from the top side of the article, wherein the method is characterised by the further steps of selectively setting the determined force, with which the pressure body is pressed against the top side of the article, on a device functioning to urge the pressure body against the top side of the article, and transporting the liquid pressed from the top side of the article to a measuring vessel with the aid of sub-pressure.

2. A method according to claim 1, characterised by transporting said liquid pressed out from the top side of the article to the measuring vessel via a space in the pressure body, said space communicating with the top side of the article via a liquid-permeable bottom of pressure body.

3. A method according to claim 1, characterised by controlling the device for pressing the pressure body against the top side of the article by means of a computer that is programmed to allow setting of a constant or varying pressure exerted by the pressure body.

4. Apparatus for measuring the liquid retention of absorbent articles that include an absorbent body having a top side which lies proximal to the wearer's skin when the article is worn, and a bottom side which is covered by a liquid-impermeable backing sheet, wherein said apparatus includes a pressure body and means for collecting liquid that gathers beneath the bottom of the pressure body, characterised in that the pressure body includes a perforated bottom and a space which is delimited downwards by said perforated bottom; in that the apparatus includes a liquid collecting vessel which is in communication with the space in said pressure body, means for generating a sub-pressure in the collecting vessel, means for measuring the amount of liquid in the collecting vessel, and means for urging the pressure body against the top side of an absorbent article at an adjustable, selective pressure, said article being placed on a fixed supportive surface centrally beneath the pressure body.

5. Apparatus according to claim 4, characterised by means for delivering liquid to the absorbent body of an absorbent article.

6. Apparatus according to claim 4, characterised by a computer for controlling the various means.

7. Apparatus according to claim 4, characterised in that the pressure body is connected to an arm that can be moved by means of a stepping motor.

8. Apparatus according to claim 4, characterised in that the collecting vessel is connected to a space in the pressure body interior which in turn, is connected to a sub-pressure source.

9. Apparatus according to claim 8, characterised in that the collecting vessel is removably connected to the pressure body by means of a tight coupling device.

10. Apparatus according to claim 4, characterised in that the pressure body is connected to the arm for pivotal movement about a horizontal axis.

* * * * *